US006652611B1

(12) United States Patent
Huang et al.

(10) Patent No.: US 6,652,611 B1
(45) Date of Patent: Nov. 25, 2003

(54) METHOD FOR MAKING ABRASIVE COMPOSITIONS AND PRODUCTS THEREOF

(75) Inventors: Yung-Hui Huang, Bel Air, MD (US); Patrick D. McGill, Darlington, MD (US); Michel J. Martin, Plainsboro, NJ (US); Minas R. Apelian, Bel Air, MD (US)

(73) Assignee: J. M. Huber Corporation, Edison, NJ (US)

( * ) Notice: Subject to any disclaimer, the term of this patent is extended or adjusted under 35 U.S.C. 154(b) by 0 days.

(21) Appl. No.: 09/641,633

(22) Filed: Aug. 18, 2000

(51) Int. Cl.⁷ .................................................. C09K 3/14
(52) U.S. Cl. ............................. 51/307; 51/293; 51/308; 51/309; 51/298; 424/49; 424/52; 424/57; 106/35
(58) Field of Search .......................... 51/307, 293, 308, 51/309, 298; 424/49, 52, 57; 106/35

(56) References Cited

U.S. PATENT DOCUMENTS

| 3,506,757 A | | 4/1970 | Salzmann | 424/52 |
|---|---|---|---|---|
| 3,934,000 A | | 1/1976 | Barth | 424/49 |
| 3,988,162 A | * | 10/1976 | Wason | 424/49 |
| 4,067,746 A | * | 1/1978 | Wason et al. | 424/49 |
| RE29,634 E | | 5/1978 | Roberts et al. | 424/57 |
| 4,098,878 A | * | 7/1978 | Baines et al. | 424/52 |
| 4,343,786 A | * | 8/1982 | Baines et al. | 424/52 |
| 4,495,167 A | | 1/1985 | Nauroth et al. | 423/339 |
| 4,701,319 A | * | 10/1987 | Woo | 424/52 |
| 4,721,615 A | * | 1/1988 | Griffith et al. | 424/57 |
| 5,310,543 A | | 5/1994 | Dawson | 424/49 |
| 5,603,920 A | | 2/1997 | Rice | 424/49 |
| 5,605,677 A | * | 2/1997 | Schumann et al. | 424/52 |
| 5,651,958 A | | 7/1997 | Rice | 424/49 |
| 5,658,553 A | | 8/1997 | Rice | 424/49 |
| 5,676,932 A | | 10/1997 | Wason et al. | 424/49 |
| 5,705,137 A | | 1/1998 | Goerl et al. | 423/335 |
| 5,891,421 A | | 4/1999 | McGill et al. | 424/49 |
| 5,989,524 A | | 11/1999 | Dromard et al. | 424/49 |

FOREIGN PATENT DOCUMENTS

| EP | 0 785 169 | 7/1997 |
|---|---|---|
| WO | WO 96/06593 | 3/1996 |
| WO | WO 97/46485 | 12/1997 |
| WO | WO 00/02814 | 1/2000 |

* cited by examiner

*Primary Examiner*—Michael Marcheschi
(74) *Attorney, Agent, or Firm*—Carlos Nieves (57) ABSTRACT

Method of making abrasive compositions comprised of water-insoluble abrasive polishing agents suspended in an aqueous medium in combination using wet grinding, and products thereof. The abrasive compositions made by the method contain appropriately sized abrasive particles provided without the need for drying or dry milling, while also providing an abrasive composition which is theologically stable, settling-resistant, and re-agglomeration resistant, even during and after transport and/or storage before end-use, such as incorporation into dentifrice formulations or other oral cleaning compositions.

23 Claims, 1 Drawing Sheet

METHOD FOR MAKING ABRASIVE COMPOSITIONS AND PRODUCTS THEREOF

BACKGROUND OF THE INVENTION

1. Field of the Invention

This invention relates to a method of making abrasive compositions, and more particularly, it relates to a method of making abrasive compositions comprised of aqueous suspensions of water-insoluble abrasive polishing agents and humectant, with abrasive particle comminution effected in post-reactor processing under wet conditions, and the products thereof.

2. Description of the Related Art

An abrasive substance has been included in conventional dentifrice compositions in order to remove various deposits, including pellicle film, from the surface of teeth. Pellicle film is tightly adherent and often contains brown or yellow pigments which impart an unsightly appearance to the teeth. While cleaning is important, the abrasive should not be so aggressive so as to damage the teeth. Ideally, an effective dentifrice abrasive material maximizes pellicle film removal while causing minimal abrasion and damage to the hard tooth tissues. Consequently, among other things, the performance of the dentifrice is highly sensitive to the abrasive polishing agent ingredient. Conventionally, the abrasive polishing material has been introduced in flowable dry powder form to dentifrice compositions, or via re-dispersions of flowable dry powder forms of the polishing agent prepared before or at the time of formulating the dentifrice.

A number of water insoluble, abrasive polishing agents have been used or described for dentifrice compositions. These abrasive polishing agents include natural and synthetic abrasive particulate materials. The generally known synthetic abrasive polishing agents include amorphous precipitated silicas, silica gels, dicalcium phosphate and its dihydrate forms, calcium pyrophosphate and precipitated calcium carbonate (PCC). Other abrasive polishing agents for dentifrices have included chalk, magnesium carbonate, zirconium silicate, potassium metaphosphate, magnesium orthophosphate, tricalcium phosphate, and the like.

Synthetically-produced precipitated silicas, in particular, have been used as abrasive components in dentifrice formulations due to their cleaning ability, relative safeness, and compatibility with typical dentifrice ingredients, such as humectants, thickening agents, flavoring agents, anti-caries agents, and so forth. As known, synthetic precipitated silicas generally are produced by the de-stabilization and precipitation of amorphous silica from soluble alkaline silicate by the addition of a mineral acid and/or acid gases under conditions in which primary particles initially formed tend to associate with each other to form a plurality of agglomerates (i.e., discrete clusters of primary particles), but without aggregation into a three-dimensional gel structure. The resulting precipitate is separated from the aqueous fraction of the reaction mixture by filtering, washing, and drying procedures, and then the dried product is mechanically comminuted in order to provide a suitable particle size.

The silica drying procedures are conventionally accomplished using spray drying, nozzle drying (e.g., tower or fountain), flash drying, rotary wheel drying, oven/fluid bed drying, and the like, which often require considerable expenditures for equipment and operating costs. A similar issue is associated with other synthetically derived polishing agents, such as silica gel and PCC.

Additionally, conventional abrasive polishing agents intended for dentifrices have required comminution in order to reduce the particle size of the dried precipitated silica product down to a size that does not feel gritty in the mouth of a dentifrice user, while, on the other hand, not being so small as to lack sufficient polishing action. That is, in conventional practice, the median particle size of the silica in the reactor formed by acidulation of a metal silicate is too large for dentifrice applications and the like. To comminute dry silica particulates, grinding and milling equipment have been used, such as a hammer or a pendulum mill used in one or multiple passes, and fine grinding has been performed, for example, by fluid energy or air-jet mill. These additional dry comminution operations entail added cost and process time.

U.S. Pat. No. 3,506,757 to Salzmann describes liquid dentifrices comprising particulate abrasive materials, stably suspended in an aqueous liquid vehicle with the aid of a polysaccharide gum as suspending agent. Similarly, PCT published application no. WO 97/46485 describes silica having a median particle size generally around 12 to 30 $\mu$m provided in the form of a suspension, which can be stabilized using a hydrocolloid, particularly naming polysaccharides such as xanthan gum, guar gum, and water-soluble cellulose ethers. U.S. Pat. No. 5,310,543 describes liquid dentifrices containing particulate siliceous abrasive cleaning agents stably suspended in a liquid medium with the aid of a polysaccharide gum and using a liquid medium specified as being substantially free from polyol-type humectants in order to obtain satisfactory rheological properties.

Among other things, rheologically stable liquid abrasive compositions containing appropriately sized abrasive particles would be desirable that could be prepared without the need for costly drying and dry milling/comminuting post-treatments.

SUMMARY OF THE INVENTION

The above and other objectives, advantages and benefits are achieved by the present invention directed to a method of making abrasive compositions comprised of aqueous suspensions of water-insoluble abrasive polishing agents in combination with humectant, with abrasive particle comminution effected during post-reactor processing under wet conditions.

Generally, the invention is directed to a method for preparing an abrasive composition, comprising the steps of introducing, into a reactor container, reaction mixture contents comprising alkali silicate and acid with inter-mixing thereof to form precipitated silica; partially dewatering of the reaction mixture after forming the precipitated silica with filtration to provide a wet or press cake; wet grinding the precipitated silica to achieve a desired median particle size in the suspended abrasive particles without any intervening step(s) of drying or dry milling being performed on the precipitated silica; and dispersing the wet-ground silica suspension with humectant either before or after the wet grinding step. Preferably, the wet milled abrasive composition prepared by this invention will have precipitated silica particles having a median particle size of about 1 micron to about 30 micron, more preferably about 3 micron to about 15 micron.

As several embodiments of the invention which meeting these objectives, the wet grinding step can be performed directly on the wet cake obtained from vacuum filtration, or, alternatively, on the press cake obtained from pressure filtration, with an intervening fluidizing step being performed on the press cake, and without any intervening drying or dehydration step being used which would reduce the water content of the cake below 5 wt % and more preferably not below about 20 wt % before performing the aforementioned wet grinding procedure on the cake.

In yet another embodiment, the invention concerns a method for preparing an abrasive composition in combination with humectant, comprising the steps of introducing, into a reactor container, reaction mixture contents comprising alkali silicate and acid with inter-mixing thereof to form precipitated silica; followed by partial dewatering of the reaction mixture after forming the precipitated silica by pressure filtration to provide a press cake and washing the press cake; then, fluidizing the precipitated-silica in the press cake by combining humectant with the precipitated silica to provide a suspension of abrasive particles containing humectant; and wet grinding the suspension of abrasive particles containing humectant, to thereby achieve the desired median particle size in the suspended abrasive particles without the need for drying and/or dry comminution processing. In this alternate embodiment, the wet grinding is performed on a fluidized version of the press cake by using humectant, instead of directly on the press cake per se.

Again, prior to the wet grinding procedure, the silica suspension, whether in press or wet cake form from pressure or vacuum filtration, or in a fluidized form after pressure filtration downstream from the silica reactor, is never dehydrated below 5 wt % water, and preferably never below about 20 wt % water, and preferably these hydraulic conditions are maintained in the abrasive composition being processed continuously from the time of silica synthesis through wet grinding of the abrasive composition.

Preferably, the wet grinding used in the above-mentioned various embodiments of the invention is accomplished by wet media milling, either as a single stage or multi-stage procedure.

Using this invention, the water-insoluble abrasive particulate product of a silica acidulation reaction can be modified to have the requisite particle size suited for oral cleaning compositions to eliminate the need for drying and comminuting dry silica solids. While not desiring to be bound to any particular theory at this time, it is postulated that the rheological properties of the abrasive compositions prepared by this invention are superior, at least in part, due the avoidance of agglomeration of particles otherwise incurred by the silica particles during conventional silica particle drying procedures. "Drying" of the silica particles, for purposes herein, means silica particles have been dehydrated to an extent that a generally dry flowable powder results as the water content is reduced below about 10 wt %. Thus, "dried" or "dry" abrasive particles have been subjected to such drying, as defined above. By contrast, the abrasive composition products made by the inventive method contain undried silica particles that retain or essentially retain the original structure and chemistry of the reactor silica.

Moreover, the method of the invention can be practiced more economically because the time as well as the equipment and operating costs otherwise required for particle drying procedures are eliminated. Additionally, the resulting abrasive compositions made by the inventive method are rheologically stable, settling-resistant, and re-agglomeration resistant, even during and after transport and/or storage before end-use. The abrasive compositions made by the inventive method are ready-to-use additives for the preparation of oral cleaning compositions, such as dentifrices, toothpastes, and the like, particularly suited as a raw material in a continuous toothpaste making process.

DETAILED DESCRIPTION OF THE PREFERRED EMBODIMENT(S)

The abrasive compositions made by the method of the present invention are highly stable, portable, storable, ready-to-use aqueous abrasive suspensions that can be readily formulated on demand with other ingredients to prepare oral cleaning compositions having a high cleaning efficacy without causing undue abrasion on tooth tissues. The essential as well as optional steps of the inventive method are described in more detail below.

Figure 1A:
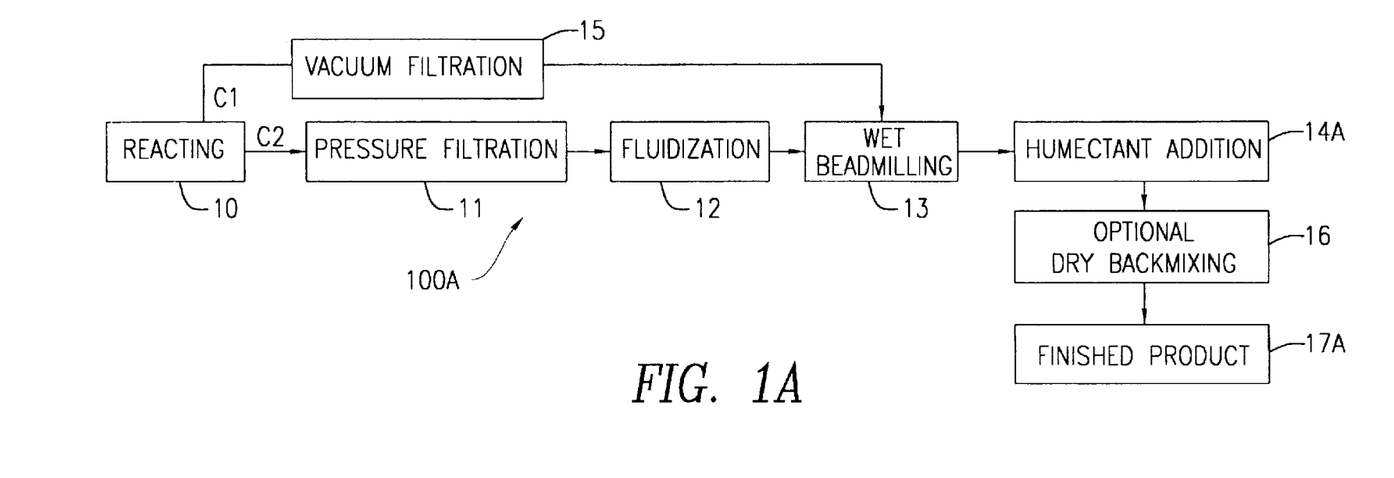
FIG. 1A is a process flow chart of method schemes for producing an abrasive slurry composition according to this invention.

Referring to FIG. 1A, a generalized processing scheme 100A is illustrated for making a silica suspension or slurry according to the invention.

In the first step of the processing scheme 100A, an acidulation reaction 10 is performed to precipitate silica. The initial acidulation reaction is performed in a reaction system equipped with suitable heating equipment. In general, the precipitated silicas made in step 10 may be prepared by a fresh water, or electrolyte solution, acidulation process wherein silica is precipitated by reaction of an alkali metal silicate and a mineral acid in aqueous solution. In the fresh water process, no electrolyte such as alum, $Na_2SO_4$, or NaCl, is present during the acidulation reaction.

A portion of the sodium silicate solution is charged to a reactor container or chamber including agitator means to provide agitation to the container contents. Preferably, about 0% to 30% of the total stoichiometric amount of sodium silicate solution is placed in the reactor container to serve as initiating nuclei for the silica. The aqueous solution of sodium silicate in the container is then preheated to a temperature in the range of about 60 to 100° C., more preferably about 80 to 95° C. Prior to introduction into the reactor container, the remaining sodium silicate is preferably preheated to about 70 to 95° C. An acid solution is preferably preheated to about 30 to 35° C.

Although sodium silicate is illustrated, it will be understood that any suitable alkali metal silicate could be used. The term "alkali metal silicate" includes all the conventional forms of alkali silicates, as for example, metal silicates, disilicates and the like. Water soluble potassium silicates and sodium silicates are particularly advantageous with the latter being preferred. It should be taken into consideration that the mole ratio of the alkali silicate, i.e., the ratio of silica to alkali metal oxide, contributes, depending on other reaction parameters, to the average pore size of the silica products. In general, acceptable silica products of this invention can be made with silicate molar ratios ($SiO_2:Na_2O$) ranging from about 1.0 to 3.5 and preferably from about 2.4 to about 3.4. The alkali silicate solution supplied to the reactor vessel 10 during various processing steps in the inventive method, as described elsewhere herein, generally can contain between about 8 to 35%, and more preferably between about 8.0% and 15.0%, by weight alkali metal silicate based on the total weight of the alkali metal silicate solution. In order to reduce the alkali silicate concentration of a source solution of alkali silicate to the above-indicated desired range, dilution water can be added to a source solution of alkali silicate before the silicate solution is fed into the reactor, or, alternatively, the dilution water can be combined in situ with the source solution of alkali silicate in the reactor 10 with agitation-mixing to formulate the desired concentration of silicate in the alkali metal silicate solution.

The acid, or acidulating agent, can be a Lewis acid or Brönsted acid, and preferably is a strong mineral acid such as sulfuric acid, hydrochloric acid, nitric acid, phosphoric acid, and so forth, and more preferably sulfuric acid, added as a dilute solution thereof (e.g., at a concentration of between about 6 to 35 wt %, more typically about 9.0 to 15.0 wt %).

Once the reactor solution and remaining reactants have reached the desired temperatures, simultaneous addition of the remaining sodium silicate solution and acid into the reactor is commenced. The sodium silicate solution and acid are metered into the reactor over an addition time of about 30 to 90 minutes. Rates of addition of the reactants depend upon the mole ratio, addition time and concentration of the silicate and the concentration of the acid. Generally, 2 mole sodium is neutralized with one mole sulfuric acid.

At the end of this co-addition period, most of the silica has precipitated and the sodium silicate addition is stopped. Addition of the acid is continued until the reactor slurry reaches the desired pH. Once the slurry pH reaches about 7.0, it is preferable to reduce the acid flow rate until the slurry pH approaches the target pH, at which point the acid flow can be stopped and manual adjustment used to reach the target slurry pH. The preferred slurry pH is approximately 4.0 to 7.0, more preferably between 4.0 to 5.0, and most preferably 4.6 ±0.1. At this juncture, the silica has precipitated to provide a mixture of the precipitated silica and the reaction liquor. Once the desired slurry pH is reached, digestion begins and the reaction temperature is raised to approximately 85–99° C., and preferably 91 to 97° C., and digestion is continued at the elevated temperature for approximately 5 to 60 minutes, and preferably for approximately 10 minutes. Acid is added during the digestion step to the extent necessary to maintain a constant pH.

After the digestion step is completed in the reactor used to implement step 10, and any subsequent pH adjustment conducted, the reaction batch is dropped. Although the above-described general protocol are preferred for synthesizing the precipitated silica to be conditioned according to this invention, it will be appreciated that other grades of precipitated silicas, such as very low to medium structure synthetic silicas in accordance with the definitions set forth in J. Soc. Cosmet. Chem., 29, 497–521 (August 1978), and Pigment Handbook: Volume 1, Properties and Economics, 2nd ed., John Wiley & Sons, 1988, p. 139–159, generally can be used in the practice of this invention.

After step 10, it is possible within one embodiment of the present invention, indicated as process route "C1" in FIG. 1A, to transmit the suspension of reactor silica, at about 2 to about 12 wt % solids, as a reactor slurry to a vacuum filtration step 15 and thereafter to the wet grinding step 13, described in greater detail below. In an alternative embodiment, the reaction mass obtained is instead processed via process route "C2" shown in FIG. 1A, where it is initially pressure filtered and washed at step 11. The pressure filter preferably is a filter press, a plate and frame filter, or a recessed chamber plate filter. The reaction mass is filtered and washed with water to reduce the $Na_2SO_4$ level to less than 5%, and preferably less than 2%, by weight (e.g., 0.5 to 1.5%). The resulting press cake generally contains about 30 to about 70 wt % solids content. The pH of the washed filter cake can be adjusted, if necessary.

After filtering and washing according to step 11 of process route C2, the press cake containing approximately 30–70 wt % solids can be reslurried with a small amount of water or fluidized with high shear in step 12. In general, the higher the shear applied, the lower the amount of water needed for fluidization in step 12, and vice versa. For example, a Cowles Model W.24x or a Motoregler Dispermat CV high shear mixer can be used to help fluidize the press cake using water. As a caveat, since the abrasive compositions of the invention are destined for oral cleaning compositions, in particular, the presence of certain conventional dispersing aids, such as polyacrylics, that otherwise might be useful for facilitating fluidizing precipitated silica filter cakes, are unacceptable in this context. The use of shear mixing during fluidization compensates for the absence of such dispersing aids. Also, the presence of those types of organic dispersants, namely, polyacrylics, have been found not to be necessary, in any event, in order to successfully practice the wet grinding operations employed in step 13 of this invention.

As indicated generally as step 13 in both FIG. 1A and 1B, the wet cake obtained directly from the vacuum filtration step 15 via process route C1, or the press cake obtained from the filter press via process route C2 including at least step 11 and step 12, or, alternatively, the press cake obtained from the filter press via process route C3 including at least step 11 and step 14B (described below), is then subjected to a wet grinding procedure to reduce the median particle size of the precipitated silica particles to respective values suited for oral cleaning compositions.

Comminution is needed because the silica particles in the abrasive suspension drawn from the reactor of step 10 generally have a median particle size (MPS) of greater than about 50 $\mu$m to about 100 $\mu$m, and more typically about 65 $\mu$m to about 85 $\mu$m. These particles sizes are unacceptable for applications such as oral cleaning compositions. Namely, smaller abrasive particles are needed so that the particles are not gritty in texture to a user, yet the particles must be large enough to provide the requisite polishing action on teeth. For oral cleaning compositions, silica particle sizes between about 1 and about 30 $\mu$m are generally required, and a median particle size of between about 3 to 15 $\mu$m is preferred in this invention.

To comminute the abrasive particles (typically agglomerates) in step 13, the wet cake received via process route C1, or the fluidized press cake received via process route C2 or C3, is fed to a wet media grinding station. No extraneous organic dispersant is added to the cake before wet grinding is performed in step 13. Either a single stage wet media mill or a multi-stage wet milling operation in step 13 can be used. For example, the multi-stage wet media grinding station, in one embodiment, can be comprised of two or more separate mills through which the cake is successively progressed. Alternatively, the multi-stage wet media grinding station can be comprised of a single mill in which the cake is fed through the single mill in multiple passes using recirculation. The amount of energy dissipated into the feed cake at each mill stage, or in each pass through a single mill in a multi-pass form of multi-stage milling, generally is kept approximately the same, although this is not necessarily required. Multi-stage wet media milling permits longer residence times to be applied.

The wet media mill types used as the mill or mills described above in the multi-stage grinding station independently can be ball mills, wet vertical media mills, wet horizontal media mills and the like. One preferred type of wet grinding mill used in the practice of this invention is a Drais Mill manufactured by Draiswerke, Inc., Mahway, N.J. The Drais mill is a vertical style media mill. The milling media used preferably are ceramic beads, e.g., zirconium oxide beads, of about 1 to 3 mm in size, which are loaded in the mills at about 40 to 80 vol %.

In keeping with an objective of this invention of reducing silica particles without the need for drying and dry milling procedures, the total amount of shearing forces applied to the wet cake or fluidized press cake during wet grinding should be sufficient to reduce the median particle size (MPS) to between about 1 to about 30 microns ($\mu$m), preferably between about 1 and about 25 microns, and more preferably between about 3 and about 15 microns. The abrasive particles in the wet milled abrasive composition have less than 1.5 wt % fraction of +325 mesh size particles.

Where processing proceeds via process routes C1 or C2 (FIG. 1A), a humecant, of the types described below, must be added with mixing (step 14A) in amounts described herein to refluidize the milled mass. For step 14A in FIG. 1A (or step 14B in FIG. 1B for that matter), a humectant is added in an amount of about 3 to about 80 wt %, preferably about 5 to about 60 wt %, more preferably about 20 to about 50 wt %, and can be even less than 30 wt % (e.g., 3 to <30 wt %), based on the total slurry weight. The humectant preferably is a polyol, such as glycerin, sorbitol, polyethylene glycol, polypropylene glycol, hydrogenated starch hydrolyzate, xylitol, lactitol, and hydrogenated corn syrup, used singly or as mixtures thereof. Glycerin and sorbitol are preferred, as used individually or in combinations. Glycerin is readily obtainable in 99.5 wt % solutions, while sorbitol is often commercially obtained as a 70 wt % solids aqueous solution. Functionally, the term humectant is customarily understood to refer to a compound which facilitates and ensures moisture retention by compositions incorporating same so as to prevent drying out of the composition upon its exposure(s) to air. Preferably, the mixing of the humectant and silica is done in a high shear mixer, such as by adding the wet cake into a mixer vessel containing the specified amount of humectant and then mixing. Examples of useful mixers in this regard are a Cowles Model W.24x, high shear mixer, a Motoregler Dispermat CV high shear mixer, or a Hockmeyer Lab 2 type disperser from Hockmeyer Equipment Company.

Figure 1B:
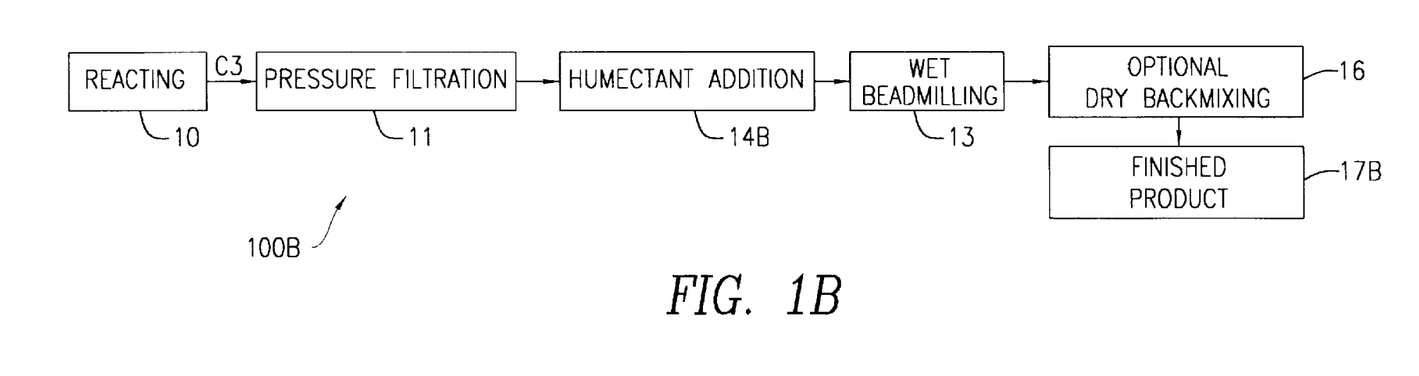
FIG. 1B is a process flow chart of another method scheme for producing an abrasive slurry composition according to this invention.

Alternatively, the milled abrasive suspension product of step 13 obtained according to process route C3 can be used as the finished product as indicated in step 17B of FIG. 1B, without the need for any further processing needed on the composition before the abrasive composition is desired to be incorporated into an oral cleaning composition. That is, in yet another alternate process route of the present invention shown as process route C3 in FIG. 1B, involves process steps 10 and 11 as described above for process route C2 in FIG. 1A, but thereafter having a different step 14B (instead of step 12), where the washed press cake of step 11 is fluidized with humectant prior to proceeding to (instead of after) the wet grinding operation in step 13. Under process route C3, the humectant, and preferably the same polyol type humectants and in the same addition range amounts described above in connection with step 14A (i.e., 3 to 80 wt % humectant, and preferably about 5 to about 60 wt %, more preferably about 20 to about 50 wt %, and can be even less than 30 wt % (e.g., 3 to <30 wt %), based on the total slurry weight), is mixed with the press cake with intense mixing, and the contents then are beadmilled in step 13 until slurry has a +325 mesh residue level of less than about 1.5% (based on dry silica weight) to provide a suspension or slurry of abrasive particles containing the humectant that has a "gelled"-like rheology that is resistant to settling. Preferably, as with step 14A, the mixing of the silica and humectant in step 14B is done in a high shear mixer, such as by adding the press cake into a mixer vessel containing the specified amount of humectant and then mixing. An example of a useful mixer for use in performing this high shear mixing is a Cowles Model W.24x high shear mixer or other mixers mentioned above in connection with step 14A. The fluidization using humectant provides an essentially uniform and thorough dispersion and distribution of the silica particles in the liquid medium (carrier).

The wet milling step 13 used in FIG. 1B is conducted under the same general conditions as described herein for step 13 of the process scheme of FIG. 1A.

The resulting abrasive suspension derived from step 13 in process flow route C3 generally comprises about 10 to about 60 weight percent of abrasive particles, from about 3 to about 80 weight percent of humectant, and from about 5 to about 50 weight percent water (preferably 5 to 30 wt. % water). The slurry derived from step 14A of process flow routes C1 and C2 has the same general composition.

In optional step 16 in either FIG. 1A or FIG. 1B, dry precipitated silica derived from a separate process, can be introduced to increase solids contents in the slurry, if desired. In any event, the finished abrasive suspension or slurries at any of steps 14A or 16 (if used) in the FIG. 1A scheme, or step 13 or 16 (if used) in the FIG. 1B scheme, can then be piped, loaded for transport stored, until needed for later usage, such in the preparation of dentifrices or other oral cleaning compositions. In this regard, the aqueous suspension of abrasive particles typically will be combined with at least one of additional water, additional humectant as needed, a binder, a fluoride ion-providing compound, a flavoring agent, a coloring agent, a whitening agent, a preservative, an anti-plaque compound, a foaming agent, and an anti-microbial agent.

The abrasive suspension 17B or 17A made according to this invention generally has a viscosity of ranging from about 100 cps to 700,000 cps, as measured at 25° C. measured on a Brookfield 1/2 RVDV II Viscometer with a T-F spindle at a speed of 5.0 rpm on a Helipath stand, and a solids settling rate of less than 30 wt % after three weeks storage at about 25° C. The resulting abrasive suspension also possesses excellent viscosity build up property. Namely, the inventive abrasive compositions possess an advantageous viscosity build up property in that it is sufficiently high to reduce requirements for thickeners or binders commonly used in the dentifrice formulations and other related ultimate uses, while not being so high as to adversely impact the useful silica loading levels due to otherwise causing an overly rapid viscosity increase upon addition.

Whether the precipitated silica to be wet milled according to the invention is introduced thereto directly as wet cake, or pre-fluidized press cake using shear or a relatively small amount of polyol humectant or water mixed with the press cake, any of these routes has been experimentally observed to yield an abrasive slurry or suspension retaining enhanced rheological stability and settling-resistance with humectant addition either before or after the wet milling operation. Additionally, the wet milled product slurry also does not experience significant re-agglomeration of the silica into larger particle sizes after the wet milling operation. Thus, the abrasive composition provided at this stage of processing, i.e., after humectant addition per step 14A of routes C1 or C2 or after wet milling per step 13 of route C3, is highly stable and particle sized appropriately so as to be portable, storable, and used on demand as a ready-to-use multi-component additive for more complex formulations such as dentifrices and other liquid oral cleaning compositions.

The high settling-resistance of the resulting abrasive compositions also makes it possible to avoid the need before end use for introduction of temporary stabilizers such as inorganic suspending agents (e.g., clays, fumed silicas) or organic binders (e.g., polysaccharides). Preferably, no polysaccharide binder is present in the inventive abrasive composition 17, or only minuscule amounts at most, viz., less than 0.20 wt % polysaccharide and more preferably less than 0.05 wt % polysaccharide is present, if at all, in the abrasive composition. Polysaccharide binders include water-soluble cellulose ethers, guar gum, and xanthan gum, and so forth, and these binder materials are not needed to rheologically stabilize and provide adequate viscosity build up property in the abrasive compositions of the present invention. When the inventive abrasive composition is ultimately combined with other requisite materials, e.g., thickeners, liquid vehicle, fluoride compounds, tartar control agents, and so forth, to form a dentifrice or other oral cleaning composition, it has been observed that the binder then can be combined with the inventive abrasive composition and the other dentifrice ingredients, such as the thickeners and liquid vehicle, without adverse impact on the rheological or silica settling properties.

A preservative, such as an anti-microbial agent (i.e., an anti-bacterial and/or anti-fungal agent), optionally can be added to the milled wet cake with mixing at step 14A as part of process route C1 or C2, or, alternatively, it can be added with mixing to the precipitated silica press cake being fluidized with humectant in step 14B as part of process route C3. The preservative in this regard can be selected, for example, from the group consisting of sodium benzoate, tetrasodium pyrophosphate, propyl-p-hydroxy-benzoate, and methyl-p-hydroxy-benzoate (methyl paraben). Effective amounts of the preservative seen to adequately prevent microbial growth are less than about 0.5 wt % based on the finished toothpaste weight. The preservative, as used in these amounts, does not impact the advantageous rheological properties of the abrasive composition.

An important aspect of this invention is that the aqueous suspension of milled abrasive particles provided by step 17A (FIG. 1A) or step 17B (FIG. 1B) can be continuously maintained at a total liquid content of at least 5 wt %, preferably at least 20 wt %, up until an additional step of incorporating said aqueous suspension of abrasive particles into a dentifrice composition or other oral cleaning composition without the need to dry the silica or perform dry milling. No drying or dry milling of the precipitated silica need occur from the time the silica is synthesized up until its incorporation into an oral cleaning composition. While not desiring to be bound to any particular theory at this time, it is postulated that drying and dry milling processes impact the surface and chemical properties of the silica particles in unpredictable or even adverse manners. The present invention avoids these impacts of drying and dry milling.

The silicas provided in the above-illustrated abrasive compositions are preferably characterized as synthetic hydrated amorphous silicas, known as silicon dioxides or $SiO_2$. These precipitated silicas can be characterized as very low to medium structure synthetic silicas in accordance with the definitions set forth in J. Soc. Cosmet. Chem., 29, 497–521 (August 1978), and Pigment Handbook: Volume 1, Properties and Economics, 2nd ed., John Wiley & Sons, 1988, p. 139–159.

In addition to the above-described step 10 methodology of precipitating the raw synthetic amorphous silicas in the reactor, the preparation of the raw silica is not necessarily limited thereto and it also can be generally accomplished in accordance with the methodologies described, for example, in prior U.S. Pat. Nos. 3,893,840, 3,988,162, 4,067,746, 4,340,583, and 5,225,177, all of which are incorporated herein by reference, as long as such methods are appropriately modified to append the post-processing treatment(s) used in at least step 13 of the inventive method. As will be appreciated by one skilled in the art, reaction parameters which affect the characteristics of the resultant precipitated silica include: the rate and timing at which the various reactants are added; the levels of concentration of the various reactants; the reaction pH; the reaction temperature; and/or the rate at which any electrolytes are added.

The precipitated silicas derived in the abrasive compositions of this invention generally have the following properties: 10% Brass Einlehner hardness values in the range between 0.5 and 30, linseed oil absorptions between about 40 to about 200 cc/100 g, RDA (Radioactive Dentin Abrasion) values between about 30 to about 200, and PCR (Pellicle Cleaning Ratio) values of 50 to 200.

Although silicas have been illustrated herein as the abrasive polishing agent component provided in the abrasive compositions being produced by this invention, it will be understood that the principles of the present invention are also considered applicable to suspensions or slurries of other water-insoluble abrasive particles that can be synthesized in a reactor without the need for any intervening drying or dry milling steps. Other such water-insoluble particles include, for example, silica gels, dicalcium phosphate or its dihydrate forms, calcium pyrophosphate and precipitated calcium carbonate (PCC).

In any event, the finished abrasive suspension or slurries at step 17A and 17B indicated in FIG. 1A and FIG. 1B, respectively, can then be piped, loaded for transport, or stored, until needed for later usage, such in the preparation of dentifrices or other oral cleaning compositions. In this regard, the aqueous suspension of abrasive particles typically will be combined with at least one of additional water, additional humectant as needed, a binder, a fluoride ion-providing compound, a flavoring agent, a coloring agent, a whitening agent, a preservative, an anti-plaque compound, a foaming agent, and an anti-microbial agent.

Examples of use of these optional dentifrice ingredients are described herein and/or, for example, in Reissue 29,634, and U.S. Pat. Nos. 5,676,932, 6,074,629, and 5,658,553, and the patents cited therein, all being incorporated herein by reference. These optional ingredients, if used, can be used at levels that are customarily seen in dentifrice formulations.

The precipitated silica component of the above-described silica suspension product (step 17A and 17B product in the Figures), when incorporated into dentifrice compositions, is present at a level of from about 10% to about 50% by weight, more preferably from about 10% to about 35% by weight, when the dentifrice is a toothpaste. Overall dentifrice or oral cleaning formulations incorporating the abrasive compositions of this invention conveniently can comprise the following possible ingredients and relative amounts thereof (all amounts in wt %): Dentifrice Formulation:

| Ingredient | Amount |
| --- | --- |
| Liquid Vehicle: | |
| humectant (s) (total) | 5–70 |
| deionized water | 5–70 |
| binder (s) | 0.5–2.0 |
| anticaries agent | 0.1–2.0 |
| chelating agent (s) | 0.4–10 |
| silica thickener* | 3–15 |

-continued

| Ingredient | Amount |
| --- | --- |
| anionic surfactant (s) | 0.5–2.5 |
| abrasive | 10–50 |
| sweetening agent | <1.0 |
| coloring agents | <1.0 |
| flavoring agent | <5.0 |
| preservative | <0.5 |

Useful silica thickeners include, for example, an amorphous precipitated silica such as Zeodent® 165 silica. Other preferred silica thickeners are Zeodent® 163 and Zeofree® 153 silicas, all available from J. M. Huber Corporation, Havre de Grace Md., USA.

EXAMPLES

The following examples are presented to illustrate the invention, but the invention is not to be considered as limited thereto. In the following examples, parts are by weight unless indicated otherwise.

Example 1

A series of batches of precipitated silicas were prepared in a reactor as follows, which thereafter were subjected to certain filtering (in all cases), fluidization (in some cases), and wet milling (in all cases) described below, without any drying or dry milling occurring, to observe the effects of the post-processing procedures that were applied.

Eight separate batches of precipitated silica were prepared as follows:

61.4 L of sodium silicate (13.3% $Na_2O$, 2.65 mole ratio of $SiO_2:Na_2O$; specific gravity of 1.123) was added to a 400 gallon stainless steel reactor jacketed for steam heating. A Lightnin A200 agitator that had been placed inside the reactor was set at 80 rpm. The reaction medium was preheated to 85° C., and this temperature was maintained for the duration of the reaction. Then, simultaneous acid and silicate flow to the reactor system was initiated and continued for a given time period. The dilute sodium silicate, preheated to 85° C., of the same concentration/composition described above was introduced to the reactor vessel at 12.25 LPM, while at the same time, a dilute sulfuric acid (11.4 wt %, SG=1.079, 39° C.) was introduced at 5.46 LPM (start acid slowly 1 L/M) to the reactor. The silicate flow was discontinued after 48 minutes of the co-addition. The acid flow was continued at 5.46 LPM until the batch pH dropped to 4.6, at which time the acid flow was stopped. The batch was then digested at 93° C. for 10 minutes, with the pH adjusted back towards 4.6 as needed throughout digestion. After digestion, the pH was manually adjust to 4.6+/−0.1 pH, and the batch was dropped. The batch was rotary vacuum filtered and washed to less than about 2% sodium sulfate.

All eight batches of wet cake silica at this stage had a median particle size of 71 microns, a +325-mesh wt % residue of about 62 wt %, and the solids content of the wet cakes was 34±1 wt %.

The batches of the wet cake, designated Runs 1, 2 and 3 were conducted directly to three different respective wet milling schemes as described below.

A vertical Drais mill, model PM5, having a 5.6 liter grinding chamber was loaded with 3.45 liters of 1.2 to 2.0 mm sized zirconia media beads having a specific gravity of 3.7. The silica wet cake of batch 1 of Run 1 was pumped through the bead mill at a flow rate of 1.1 liters/min. with the bead mill set at 1590 r.p.m. The silica wet cake of batch 2 of Run 1 was separately pumped through the bead mill under the same above-described milling conditions at a flow rate of 0.6 liters/min. The silica wet cake of batch 3 of Run 1 was separately pumped through the bead mill at a flow rate of 2.5 liters/min. for three passes. The silica wet cake of batch 4 of Run 1 was separately pumped through the bead mill at a flow rate of 1.0 liters/min for two passes. The results, insofar as the median particle size and +325 mesh % residues of the wet milled silica particles in the slurries of respective batches 1 to 4 are summarized in Table 1 below.

For separate batches 5 and 6 of Run 2, the wet cake obtained from the vacuum filter was pumped to a filter press for dewatering at 90 p.s.i. on a plate and frame type filter. The press cakes obtained had a solids content of about 50 wt %. These batches then were each fluidized by mixing 100 lbs. of the 50 wt % solids cake with 100 lbs. of sorbitol (70%) to form 1:1:2 compositions, respectively, of silica-:water:sorbitol slurry. Mixing of the press cake and sorbitol humectant was obtained by using a Cowles high shear disperser Model W.24x.

Then, the three fluidized slurries were each subjected to wet milling, where the milling conditions were similar to those reported above for Run 1 except that the slurries each had a 25 wt % silica content. A slurry feed flow rate through the mill of 2.5 liters/min. for each of batches 5 and 6. The fluidized slurry of batch 5 was recycled/passed through the mill two successive times, while the fluidized slurry of batch 6 was passed through the mill only a single time. The results, insofar as the median particle size and +325 mesh % residues of the wet milled silica particles in the respective slurries of batches 5 and 6 of Run 2 are summarized in Table 1 below.

For separate batches 7 and 8 of Run 3, the wet cake obtained from the vacuum filter was pumped to a filter press for dewatering at 90 p.s.i. on a plate and frame type filter. The press cakes obtained had a solids content of about 50 wt %. The pressed cake was fluidized by mixing 2141.3 g of 50 wt. % solids press cake with 699.7 g of sorbitol (70 wt. %) to form a 1.5:1.5:1 composition of silica:water:sorbitol, respectively. Mixing of the press cake and sorbitol humectant was obtained by using a Hockmeyer mixer Model Lab 2.

Then the two fluidized silica press cakes were each subjected to wet milling. A Premier bead mill, model HML-1.5, having a 1.5 liter grinding chamber was loaded with 1.2 liters of 0.6–1.0 mm sized zirconia media beads having a specific gravity of 3.7. The bead mill speed was set at 1000 ft/min. The fluidized press cake of batch 7, Run 3, was pumped through the bead mill at a flow rate of 0.26 LPM. The fluidized press cake of batch 8, Run 3, was pumped through the bead mill at a flow rate of 0.63 LPM.

The results, insofar as the median particle size and +325 mesh % residues of the wet milled silica particles in the respective slurries of batches 7–8 of Run 3 are summarized in Table 1 below.

For separate batch 9, 24.8 L of sodium silicate (13.3% $Na_2O$, 2.65 mole ratio of $SiO_2:Na_2O$; specific gravity of 1.123) and 1.78 kg $Na_2SO_4$ was added to a 400 gallon stainless steel reactor jacketed for steam heating. A Lightnin A200 agitator that had been placed inside the reactor was set at 60 rpm. The reaction medium was preheated to 93° C., and this temperature was maintained for the duration of the reaction. Then, simultaneous acid and silicate flow to the reactor system was initiated and continued for a given time period. The dilute sodium silicate, preheated to 88° C., of the same concentration/composition described above was introduced to the reactor vessel at 13.00 LPM, while at the same time, a dilute sulfuric acid (11.4 wt %, SG=1.079, 39° C.) was introduced at 4.74 LPM (start acid slowly 1 L/M) to the reactor. The silicate flow was discontinued after 47 minutes of the co-addition. The acid flow was continued at 4.74 LPM until the batch pH dropped to 7.0. At a batch pH of 7.0, the acid flow was reduced to 1.5 LPM, and the acid addition continued until the pH approached 4.6, at which time the acid flow was close to 4.6 and was then manually adjust to a target of 4.6+/−0.1 pH. The batch was then digested at 98° C. for 10 minutes, with the pH adjusted back towards 4.6 as needed throughout digestion. After digestion, the pH was manually adjust to 4.6+/−0.1 pH, and 1/2 of the batch was dropped and agitated, and then pumped to a filter press for filtering on a plate and frame type filter. The batch was dewatered at 40 p.s.i. and was washed to remove most (to <2.0 wt %) of the reaction by-product (sodium sulfate). The press cake obtained had a solids content of 52.35 wt %., a median particle size of 69.5 microns, and a +325-mesh wt % residue of 56.73 wt %.

The batch then was fluidized by mixing 3031.2 g of the 52.35 wt % solids press cake with 968.8 g of glycerin (99.5%) to form a 1.65:1.5:1 composition, respectively, of silica:water:glycerin slurry. Mixing of the press cake and glycerin humectant was obtained by using a Hockmeyer mixer Model Lab 2.

Then, the fluidized press cake was subjected to wet milling. A Premier bead mill, model HML-1.5, having a 1.5 liter grinding chamber was loaded with 1.2 liters of 0.6–1.0 mm sized zirconia media beads having a specific gravity of 3.7. The fluidized silica slurry of batch 9, Run 4 was pumped through the bead mill at a flow rate of 0.3 liters/min. with the bead mill set at 2000 ft/min.

For comparison, the other 1/2 of batch 9 produced as described above was spray dried with an inlet temperature of about 480° C. to a target moisture level of 7.0 wt. %.

The results, insofar as the median particle size and +325 mesh % residues of the wet milled silica particles in the slurry of batch 9 of Run 4 are summarized in Table 1 below together with the results for batches 1–4 of Run 1, batches 5–6 of Run 2 and batches 7–8 of Run 3.

TABLE 1

| Run | Batch | No. passes | Flow Rate (L/min) | MPS ($\mu$m) | +325 Residues (wt %) |
|---|---|---|---|---|---|
| 1 | 1 | 1 | 1.1 | 11.91 | 1.04 |
| 1 | 2 | 1 | 0.6 | 4.02 | 0.015 |
| 1 | 3 | 3 | 2.5 | 6.80 | 0.091 |
| 1 | 4 | 2 | 2.5 | 7.29 | 0.130 |
| 2 | 5 | 1 | 2.5 | 10.62 | 0.90 |
| 2 | 6 | 2 | 1.0 | 6.76 | 0.049 |
| 3 | 7 | 1 | 0.26 | 6.19 | 1.87 |
| 3 | 8 | 1 | 0.63 | 5.48 | 1.36 |
| 4 | 9 | 1 | 0.3 | 4.56 | 1.75 |

The silica properties described herein were measured as follows.

The precipitated silicas used in the dentifrice compositions of this invention have a median particle size (MPS) measured using a Microtrac II apparatus, Leeds and Northrup.

325 mesh residue (+325) is measured utilizing a U.S. Standard Sieve No. 325, with 44 micron or 0.0017 inch openings (stainless steel wire cloth) by weighing a 10.0 gram sample to the nearest 0.1 gram into the cup of the 1 quart Hamilton mixer Model No. 30, adding approximately 170 ml of distilled or deionized water and stirring the slurry for at least 7 min. The mixture is transferred onto the 325 mesh screen; washing out the cup and add washings onto the screen. A water spray is adjusted to 20 psi and sprayed directly on the screen for two minutes. (Spray head is held about four to six inches above the screen.) The residue is washed to one side of the screen and transferred by washing into an evaporating dish using distilled or deionized water. After letting the residue sit for two to three minutes, the clear water is decanted. The residue is dried (convection oven @ 150° C. for approx. 15 min.) cooled and weighed on analytical balance.

Example 2

Toothpaste formulations were prepared using the inventive silica wet cake of batch 3, fluidized press cakes of batches 5 and 9. Comparison toothpaste formulations, referenced as "3C" and "9C" respectively, were prepared with batch 3 wet cake and batch 9 press cake that had been spray dried and milled for comparison purpose. The spray drying used on the comparison samples involved drying wet cake to 7.0% $H_2O$, ±1% using an atomizing spray drying means having an inlet temperature at 480° C. The spray dried samples of the comparative silica were then Hammermilled to 8–14 $\mu$m. Properties for these products are given in Table 2A below.

TABLE 2A

| Batch Undried/Dry | Batch 3 undried | Batch 3C Dry | Batch 5 undried | Batch 9 undried | Batch 9C Dry |
|---|---|---|---|---|---|
| % Moisture | — | 6.5 | — | — | 4.6 |
| % 325 Mesh | 0.091 | 0.00 | 0.13 | 1.75 | 0.10 |
| 5% pH | — | 7.36 | — | — | 7.52 |
| % $Na_2SO_4$ | — | 0.74 | — | — | <0.35 |
| MPS, $\mu$m | 6.80 | 6.61 | 7.29 | 4.56 | 10.40 |
| TAPPI Brightness | — | 97.3 | — | — | 94.2 |
| CTAB Surface Area, $m^2/g$ | — | 44 | — | — | 26 |
| BET Surface Area, $m^2/g$ | — | 162 | — | — | 240 |
| Oil Absorption, cc/100 g | — | 84 | — | — | 65 |
| Hg Intrusion, mL/g | — | 2.4826 | — | — | — |
| Einlehner Abrasion, mg (dry product) | — | 4.93 | — | — | 10.24 |
| Einlehner Abrasion, mg (wet cake) | 3.6 | — | — | 8.65 | — |

Toothpaste formulations were prepared to demonstrate the ready-to-use on demand capabilities of the inventive abrasive slurry compositions. A portion of silica wet cake 3, fluidized press cakes 5 and 9, as described above, were fluidized with either glycerin or sorbitol in amounts as described in Table 2B below, and thereafter dentifrices were formulated with these fluidized silica wet cakes as described in Table 2C below. For comparison, portions of the dried and milled silica described above were separately incorporated in toothpaste formulations. Properties of these dentifrice formulations are given in Table 2D below.

To prepare the dentifrices, the following procedure was followed. Additional humectant (glycerin, sorbitol) for combination with the humectant amount being introduced via the abrasive-humectant suspension to achieve the full amount of humectant needed for the dentifrice, sodium carboxymethyl cellulose, and polyethylene glycol are mixed together to form a first admixture. The deionized water amount not included in the abrasive-humectant suspension, sodium fluoride, tetrasodium pyrophosphate and sodium saccharin are also mixed together until these ingredients are dissolved to form a second admixture. These two mixtures are combined with stirring. Thereafter, color is optionally added and the combined mixture is stirred with a Lightnin mixer to obtain a "Pre-mix".

The "Pre-mix" is placed in a Ross mixer (Model 130 LDM) and the abrasive-humectant suspension, silica thickener and any required $TiO_2$ are added and mixed without vacuum. A 30 inch vacuum is then drawn and the resultant admixture is stirred for approximately 15 minutes. Lastly, sodium lauryl sulfate and flavor are added and the admixture is stirred for approximately 5 minutes at reduced mixing speed.

The resulting dentifrice composition is sealed in toothpaste tubes and held under appropriate conditions for later testing. The compositions had a pH of about 7.

TABLE 2B

| | Slurry Component Make-up | | | | |
|---|---|---|---|---|---|
| Abrasive slurry No. | 1 | 2 | 3 | 4 | 5 |
| Sorbitol, 70%, g | 94 | — | 38 | — | — |
| Glycerin, 99.5%, g | — | — | — | 968.8 | — |
| Batch 3 wet cake, g | 272.3 | — | — | — | — |
| Batch 3C, dry & milled, g | 103.7 | 20 | — | — | — |
| Batch 4 press cake, g | — | — | 38 | — | — |
| Batch 9 press cake, g | — | — | — | 3031.2 | — |
| Batch 9C, dry & mill, g | — | — | — | — | 20 |
| Total | 470 | 20 | 76 | 4000 | 20 |
| 325 Residue, % | 1.55 | — | 0.13 | 1.75 | — |

TABLE 2C

| Toothpaste Formula # | 1 | 2 | 3 | 4 | 5 |
|---|---|---|---|---|---|
| Glycerin, 99.5%, g | 11.6 | 11.6 | 11.6 | 0 | 11.6 |
| CMC-7MF, g | 1.4 | 1.4 | 1.4 | 1.4 | 1.4 |
| Sorbitol, 70%, g | 27.86 | 38.257 | 0.257 | 38.257 | 38.257 |
| Deionized water, g | 7.4 | 25 | 7 | 8.71 | 25 |
| Sodium Fluoride, g | 0.243 | 0.243 | 0.243 | 0.243 | 0.243 |
| Sodium Saccharin, g | 0.3 | 0.3 | 0.3 | 0.3 | 0.3 |
| Sodium Benzoate, g | 0.5 | 0.5 | 0.5 | 0.5 | 0.5 |
| $TiO_2$, g | 0.5 | 0.5 | 0.5 | 0.5 | 0.5 |
| Abrasive Slurry No. | | | | | |
| 1, g | 48 | — | — | — | — |
| 2, g | — | 20 | — | — | — |
| 3, g | — | — | 76 | — | — |
| 4, g | — | — | — | 47.89 | — |
| 5, g | — | — | — | — | 20 |
| Sodium lauryl sulfate, g | 1.2 | 1.2 | 1.2 | 1.2 | 1.2 |
| Flavor, g | 1 | 1 | 1 | 1 | 1 |
| Total | 100.00 | 100.00 | 100.00 | 100.00 | 100.00 |

CMC-7MXF is carboxymethylcellulose available from Aqualon, division of Hercules Corporation, Wilmington, DE.

Toothpaste formulated with the inventive silica slurry compositions had good viscosity and aesthetic properties.

The silica, silica slurry, and toothpaste properties described herein were measured as follows, unless indicated otherwise.

The Brass Einlehner (BE) Abrasion test used to measure the hardness of the precipitated silicas reported in this application involves an Einlehner AT-1000 Abrader generally used as follows: (1) a Fourdrinier brass wire screen is weighed and exposed to the action of a 10% aqueous silica suspension for a fixed length of time; (2) the amount of abrasion is then determined as milligrams brass lost from the Fourdrinier wire screen per 100,000 revolutions. The result, measured in units of mg loss, can be characterized as the 10% brass Einlehner (BE) abrasion value.

The oil absorption values are measured using the rubout method. This method is based on a principle of mixing linseed oil with a silica by rubbing with a spatula on a smooth surface until a stiff putty-like paste is formed. By measuring the quantity of oil required to have a paste mixture which will curl when spread out, one can calculate the oil absorption value of the silica—the value which represents the volume of oil required per unit weight of silica to saturate the silica sorptive capacity. Calculation of the oil absorption value was done as follows:

$$\text{Oil absorption} = \frac{\text{cc oil absorbed}}{\text{weight of silica, grams}} \times 100$$

$$= \text{cc oil}/100 \text{ gram silica}$$

The surface area of the precipitated silica reported herein is determined the BET nitrogen adsorption method of Brunaur et al., J. Am. Chem. Soc., 60, 309 (1938).

To measure brightness, fine powder materials are pressed into a smooth surfaced pellet are evaluated using a Technidyne Brightmeter S-5/BC. This instrument has a dual beam optical system where the sample is illuminated at an angle of 45°, and the reflected light viewed at 0°. It conforms to TAPPI test methods T452 and T646, and ASTM Standard D985. Powdered materials are pressed to about a 1 cm thick pellet with enough pressure to provide a pellet surface that is smooth and flat and without loose particles or gloss.

The total pore volume (Hg) is measured by mercury porosimetry using a Micromeritics Autopore II 9220 apparatus. The pore diameters can be calculated by the Washburn equation employing a contact angle Theta ($\theta$) equal to 130° and a surface tension gamma equal to 484 dynes/cm. This instrument measures the void volume and pore size distribution of various materials. Mercury is forced into the voids as a function of pressure and the volume of the mercury

TABLE 2D

| Toothpaste Formula # | 1 | 2 | 3 | 4 | 5 |
|---|---|---|---|---|---|
| Initial Viscosity, 24 hr. | 820,000 | 320,000 | 160,000 | 320,000 | 240,000 |
| 1 Wk Viscosity | 800,000 | 350,000 | 220,000 | 450,000 | 280,000 |
| 3 Wk Viscosity | 1,010,000 | 410,000 | 220,000 | 300,000 | 430,000 |
| 6 Wk Viscosity | 920,000 | 350,000 | — | — | — |
| 25% pH | 7.9 | 8.91 | 6.62 | 6.55 | 6.53 |
| Specific Gravity | 1.292 | 1.258 | 1.225 | 1.279 | 1.296 |
| L value | 89.5 | 90.7 | 90.6 | 89.0 | 84.5 |
| $a_L$ | −2.2 | −2.1 | −1.7 | −1.5 | −1.3 |
| $b_L$ | 3.1 | 2.6 | 2.3 | 2.3 | 1.6 | intruded per gram of sample is calculated at each pressure setting. Total pore volume expressed herein represents the cumulative volume of mercury intruded at pressures from vacuum to 60,000 psi. Increments in volume (cm$^3$/g) at each pressure setting are plotted against the pore radius or diameter corresponding to the pressure setting increments. The peak in the intruded volume versus pore radius or diameter curve corresponds to the mode in the pore size distribution and identifies the most common pore size in the sample. Specifically, sample size is adjusted to achieve a stem volume of 30–50% in a powder penetrometer with a 5 ml bulb and a stem volume of about 1.1 ml. Samples are evacuated to a pressure of 50 µm of Hg and held for 5 minutes. Mercury fills the pores from 1.5 to 60,000 psi with a 10 second equilibrium time at each of approximately 150 data collection points.

CTAB external surface area of silica is determined by absorption of CTAB (cetyltrimethylammonium bromide) on the silica surface, the excess separated by centrifugation and determined by titration with sodium lauryl sulfate using a surfactant electrode. The external surface of the silica is determined from the quantity of CTAB adsorbed (analysis of CTAB before and after adsorption). Specifically, about 0.5 g of silica is placed in a 250-ml beaker with 100.00 ml CTAB solution (5.5 g/L), mixed on an electric stir plate for 1 hour, then centrifuged for 30 minutes at 10,000 rpm. One ml of 10% Triton X-100 is added to 5 ml of the clear supernatant in a 100-ml beaker. The pH is adjusted to 3.0–3.5 with 0.1 N HCI and the specimen is titrated with 0.0100 M sodium lauryl sulfate using a surfactant electrode (Brinkmann SURl5Ol-DL) to determine the endpoint.

Moisture is the measured sample weight loss at 105° C. for 2 hours. The pH values of the reaction mixtures (5 weight % slurry) encountered in the present invention can be monitored by any conventional pH sensitive electrode.

The toothpaste viscosity is measured utilizing a Brookfield Viscometer Model RVT equipped with a Helipath T-F spindle and set to 5 rpm by measuring the viscosity of the toothpaste at 25° C. at three different levels as the spindle descends through the toothpaste test sample and averaging the results. Brookfield viscosity is expressed in centipoise (cP).

Toothpaste color (L, $a_L$, $b_L$) is measured utilizing a Gardner XL-835 Colorimeter. Specifically, two 38×75×1 mm microscope slides are placed on a flat surface. A plexiglass spacer (38×75×3 mm thick with a 24×47 mm cut-out open space) is placed on top of one of the slides. Toothpaste gel is squeezed into the open area of the plexiglass spacer and the second microscope slide is placed on top of the spacer with enough pressure (by hand) to eliminate excess air and toothpaste. The slide is placed on the calorimeter back port opening and three readings are taken at different specimen spacer locations and averaged. The specimen should have no visible air bubbles.

It will be understood that various changes in the details, materials, and arrangements of the parts which have been described and illustrated herein in order to explain the nature of this invention may be made by those skilled in the art without departing from the principles and scope of the invention as expressed in the following claims.

What is claimed is:

1. A method for preparing an abrasive slurry composition, comprising the steps of introducing, into a reactor container, reaction mixture contents comprising reactants effective for forming water-insoluble abrasive amorphous silica particles via precipitation; wet grinding the abrasive amorphous silica particles and in the absence of prior drying of said amorphous silica particles between said forming step and said wet grinding step; and, before or after said wet grinding, fluidizing the abrasive amorphous silica particles by combining humectant with the abrasive amorphous silica particles with mixing effective to provide an abrasive slurry composition.

2. The method according to claim 1, wherein said abrasive silica particles are polishing agents selected from the group consisting of precipitated silica and silica gels.

3. The method according to claim 1, wherein the abrasive particles comprise a plurality of precipitated silica particles having a median particle size of about 1 micron to about 30 micron.

4. The method according to claim 1, further comprising, before said wet grinding step, the additional step of vacuum filtering the reaction mixture to form a wet cake of the abrasive particles, and wherein said fluidizing step is performed after wet grinding said wet cake.

5. A method for preparing an abrasive slurry composition, comprising the steps of:
 introducing, into a reactor container, reaction mixture contents comprising alkali silicate and acid with intermixing thereof to form a suspension of particles of precipitated silica;
 partially dewatering the reaction mixture after forming the precipitated silica particles with filtering to provide a filter cake;
 fluidizing the precipitated silica particles in the filter cake by combining water with the precipitated silica particles with mixing effective to provide an aqueous suspension of precipitated silica particles;
 wet grinding the aqueous suspension of precipitated silica particles; and
 refluidizing the precipitated silica particles by combining humectant with the precipitated silica particles with mixing effective to provide a suspension of abrasive precipitated silica particles.

6. The method according to claim 5, wherein the wet grinding step is performed without any prior drying of the precipitated silica which would reduce the water content thereof below 20 wt %.

7. The method according to claim 5, wherein the wet grinding step comprises wet media milling.

8. The method according to claim 5, wherein the abrasive slurry composition comprises a plurality of precipitated silica particles having a median particle size of about 1 micron to about 30 micron.

9. The method according to claim 5, wherein the abrasive slurry composition comprises a plurality of precipitated silica particles having a median particle size of about 3 micron to about 15 micron.

10. The method according to claim 5, further comprising a step of combining the abrasive composition with at least one of additional water, binder, fluoride ion-providing compound, flavoring agent, coloring agent, whitening agent, preservative, tarter control compound, foaming agent, or anti-microbial agent.

11. A method for preparing an abrasive slurry composition, comprising the steps of:
 introducing, into a reactor container, reaction mixture contents comprising alkali silicate and acid with intermixing thereof to form particles of precipitated silica;
 partially dewatering the reaction mixture after forming the precipitated silica particles by filtering to provide a filter cake;
 fluidizing the precipitated silica in the filter cake by combining humectant with the precipitated silica with mixing effective to provide a suspension of precipitated particles containing humectant; and wet grinding said suspension of precipitated particles containing humectant to provide an abrasive slurry composition.

12. The method according to claim 11, wherein the humectant is present in the abrasive slurry composition in an amount of about 20 to about 50 wt %.

13. The method according to claim 11, wherein said humectant is a polyol.

14. The method according to claim 11, wherein said humectant is selected from the group consisting of glycerin, sorbitol, polyethylene glycol, polypropylene glycol, hydrogenated starch hydrolyzate, xylitol, lactitol, and hydrogenated corn syrup, used singly or as mixtures thereof.

15. The method according to claim 11, further comprising adding a preservative to the suspension of precipitated silica particles with mixing prior to or after said wet grinding step.

16. The method according to claim 15, wherein the preservative is selected from the group consisting of sodium benzoate, tetrasodium pyrophosphate, propyl-p-hydroxy-benzoate, and methyl-p-hydroxy-benzoate (methyl paraben).

17. The method according to claim 11, wherein said filtering step provides a liquid suspension of the precipitated particles, and further comprising continuously maintaining the liquid suspension of precipitated silica particles at a total liquid content of at least 20 wt % after said filtering step up until performing an additional step of incorporating said suspension of precipitated silica particles into a dentifrice composition.

18. The method according to claim 11, further comprising a step of combining the suspension of precipitated particles with at least one of additional water, binder, fluoride ion-providing compound, flavoring agent, coloring agent, whitening agent, preservative, tarter control compound, foaming agent, or anti-microbial agent.

19. The method according to claim 11, wherein said wet grinding comprises wet media milling the suspension of precipitated silica particles after introducing the humectant and before the suspension of precipitated silica particles is incorporated into a dentifrice composition.

20. The method according to claim 11, wherein said filtering is performed by pressure filtration.

21. The abrasive composition product of the method of claim 1.

22. The abrasive composition product of the method of claim 5.

23. The abrasive composition product of the method of claim 11.

* * * * *